United States Patent
Ninomiya et al.

(10) Patent No.: US 7,446,223 B2
(45) Date of Patent: Nov. 4, 2008

(54) PALLADIUM-CONTAINING CATALYST AND METHOD FOR PRODUCING SAME

(75) Inventors: Wataru Ninomiya, Hiroshima (JP); Yoshiyuki Himeno, Hiroshima (JP); Yuji Fujimori, Hiroshima (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 25 days.

(21) Appl. No.: 11/628,214

(22) PCT Filed: Jun. 2, 2005

(86) PCT No.: PCT/JP2005/010139

§ 371 (c)(1), (2), (4) Date: Dec. 1, 2006

(87) PCT Pub. No.: WO2005/118134

PCT Pub. Date: Dec. 15, 2005

(65) Prior Publication Data

US 2007/0238903 A1 Oct. 11, 2007

(30) Foreign Application Priority Data

Jun. 4, 2004 (JP) ............................. 2004-167120

(51) Int. Cl.
C07C 51/14 (2006.01)
C07C 51/16 (2006.01)
C07C 45/34 (2006.01)

(52) U.S. Cl. ...................... 562/522; 562/546; 568/446; 568/470

(58) Field of Classification Search ................ 502/339; 568/446, 470; 562/522, 546
See application file for complete search history.

(56) References Cited

U.S. PATENT DOCUMENTS 4,310,709 A * 1/1982 Rebafka ..................... 568/687
5,283,379 A * 2/1994 Saiki et al. .................. 570/156
5,679,875 A 10/1997 Aoyama et al.
6,278,031 B1 * 8/2001 Brocker et al. .............. 568/906
6,559,333 B1 5/2003 Brunelle et al.

FOREIGN PATENT DOCUMENTS

| CN | 1083040 A | 3/1994 |
|---|---|---|
| CN | 1302291 A | 7/2001 |
| JP | 56 59722 | 5/1981 |
| JP | 4 90853 | 3/1992 |
| JP | 10 204029 | 8/1998 |
| JP | 2003 53189 | 2/2003 |
| JP | 2004 121965 | 4/2004 |
| WO | 02 083299 | 10/2002 |

OTHER PUBLICATIONS

U.S. Appl. No. 11/719,461, filed May 16, 2007, Himeno, et al.
U.S. Appl. No. 11/628,214, filed Dec. 1, 2006, Ninomiya, et al.

* cited by examiner

Primary Examiner—Sikarl A Witherspoon
(74) Attorney, Agent, or Firm—Oblon, Spivak, McClelland, Maier & Neustadt, P.C.

(57) ABSTRACT

The present invention provides: a palladium-containing catalyst which is used for highly selectively or highly productively producing an $\alpha,\beta$-unsaturated aldehyde and an $\alpha,\beta$-unsaturated carboxylic acid from an olefin or in that way producing an $\alpha,\beta$-unsaturated carboxylic acid from an $\alpha,\beta$-unsaturated aldehyde; a method for producing the catalyst; and a method for highly selectively or highly productively producing an $\alpha,\beta$-unsaturated aldehyde and an $\alpha,\beta$-unsaturated carboxylic acid from an olefin or in that way producing an $\alpha,\beta$-unsaturated carboxylic acid from an $\alpha,\beta$-unsaturated aldehyde. In particular, the present invention resides in a palladium-containing catalyst comprising 0.001 to 0.40 mole of tellurium metal to 1.0 mole of palladium metal. This catalyst can be preferably produced by a method having a step of reducing a compound containing palladium atom in its oxidized state and tellurium atom in its oxidized state by a reducing agent.

12 Claims, No Drawings

PALLADIUM-CONTAINING CATALYST AND METHOD FOR PRODUCING SAME

TECHNICAL FIELD

The present invention relates to a palladium-containing catalyst for producing an α,β-unsaturated aldehyde and an α,β-unsaturated carboxylic acid from an olefin and a method for producing the same. Further, the present invention relates to a method for producing an α,β-unsaturated aldehyde and an α,β-unsaturated carboxylic acid.

Furthermore, the present invention relates to a palladium-containing catalyst for producing an α,β-unsaturated carboxylic acid from an α,β-unsaturated aldehyde and a method for producing the same. Further, the present invention relates to a method for producing an α,β-unsaturated carboxylic acid.

BACKGROUND ART

There has been proposed, for example, a catalyst containing palladium metal and another metal (lead, bismuth, thallium or the like) in Patent Document 1, as a palladium-containing catalyst for producing an α,β-unsaturated aldehyde and an α,β-unsaturated carboxylic acid through liquid-phase oxidation of an olefin with molecular oxygen.

Patent Document 1: Japanese Patent Application Laid-Open No. 56-59,722.

DISCLOSURE OF THE INVENTION

Problem to be Solved by the Invention

When the present inventors produced methacrolein and methacrylic acid from isobutylene by using the palladium-containing catalyst produced according to the methods described in Examples of Patent Document 1, it was found that various by-products (acetone, acetic acid, methallyl methacrylate and the like), polymers and oligomers were produced in large amount in addition to the products described in Patent Document 1. In Patent Document 1, these by-products, polymers and oligomers were not captured, and hence the actual selectivities to methacrolein and methacrylic acid in view of these by-products were found to be lower than those described in Examples of Patent Document 1. Consequently, the selectivities to an α,β-unsaturated aldehyde and an α,β-unsaturated carboxylic acid of the palladium-containing catalyst produced by the methods described in Patent Document 1 was not sufficient yet, and hence, a catalyst for producing an α,β-unsaturated aldehyde and an α,β-unsaturated carboxylic acid in higher selectivity has been desired.

Further, a catalyst for producing an α,β-unsaturated aldehyde and an α,β-unsaturated carboxylic acid in high activity and high productivity has been desired.

This palladium-containing catalyst can also function as a catalyst for producing an α,β-unsaturated carboxylic acid through liquid-phase oxidation of an α,β-unsaturated aldehyde with molecular oxygen, however, it was also found that polymers and oligomers were produced in large amount in the production of the α,β-unsaturated carboxylic acid like as the case described above, and hence, a catalyst for producing an α,β-unsaturated carboxylic acid in higher selectivity has been desired.

Further, a catalyst for producing an α,β-unsaturated carboxylic acid in high activity and high productivity has been desired.

Therefore, it is an object of the present invention to provide a palladium-containing catalyst for producing an α,β-unsaturated aldehyde and an α,β-unsaturated carboxylic acid from an olefin in high selectivity or in high productivity, a method for producing the same and a method for producing an α,β-unsaturated aldehyde and an α,β-unsaturated carboxylic acid in high selectivity or in high productivity.

It is a further object of the present invention to provide a palladium-containing catalyst for producing an α,β-unsaturated carboxylic acid from an α,β-unsaturated aldehyde in high selectivity or in high productivity, a method for producing the same and a method for producing an α,β-unsaturated carboxylic acid in high selectivity or in high productivity.

Means for Solving Problem

The present invention resides in a palladium-containing catalyst for producing an α,β-unsaturated aldehyde and an α,β-unsaturated carboxylic acid from an olefin, comprising 0.001 to 0.40 mole of tellurium metal to 1.0 mole of palladium metal. It is preferable that the palladium metal and the tellurium metal be supported on a carrier. Further, the present invention resides in a method for producing an α,β-unsaturated aldehyde and an α,β-unsaturated carboxylic acid through liquid-phase oxidation of an olefin with molecular oxygen by using the foregoing palladium-containing catalyst.

The present invention resides in a palladium-containing catalyst for producing an α,β-unsaturated carboxylic acid from an α,β-unsaturated aldehyde, comprising 0.001 to 0.40 mole of tellurium metal to 1.0 mole of palladium metal. It is preferable that the palladium metal and the tellurium metal be supported on a carrier. Further, the present invention resides in a method for producing an α,β-unsaturated carboxylic acid through liquid-phase oxidation of an α,β-unsaturated aldehyde with molecular oxygen by using the foregoing palladium-containing catalyst.

Further, the present invention resides in a method for producing the foregoing palladium-containing catalyst, comprising a step of reducing a compound containing palladium atom in its oxidized state and tellurium atom in its oxidized state by a reducing agent.

Furthermore, the present invention resides in a method for producing the foregoing palladium-containing catalyst, comprising a step of reducing a compound containing palladium atom in its reduced state and tellurium atom in its oxidized state by a reducing agent.

Effect of the Invention

By the palladium-containing catalyst of the present invention, an α,β-unsaturated aldehyde and an α,β-unsaturated carboxylic acid can be produced in high selectivity or in high productivity in the case that the α,β-unsaturated aldehyde and the α,β-unsaturated carboxylic acid are produced from an olefin. Further, by the method for producing the palladium-containing catalyst of the present invention, a palladium-containing catalyst which can produce an α,β-unsaturated aldehyde and an α,β-unsaturated carboxylic acid in high selectivity or in high productivity in the case that the α,β-unsaturated aldehyde and the α,β-unsaturated carboxylic acid are produced from an olefin can be produced. Furthermore, by the method for producing an α,β-unsaturated aldehyde and an α,β-unsaturated carboxylic acid through liquid-phase oxidation of an olefin with molecular oxygen by using the palladium-containing catalyst of the present invention, an α,β-unsaturated aldehyde and an α,β-unsaturated carboxylic acid can be produced in high selectivity or in high productivity.

By the palladium-containing catalyst of the present invention, an α,β-unsaturated carboxylic acid can be produced in high selectivity or in high productivity in the case that the α,β-unsaturated carboxylic acid is produced from an α,β-unsaturated aldehyde. Further, by the method for producing the palladium-containing catalyst of the present invention, a palladium-containing catalyst which can produce an α,β-unsaturated carboxylic acid in high selectivity or in high productivity in the case that the α,β-unsaturated carboxylic acid is produced from an α,β-unsaturated aldehyde can be produced. Furthermore, by the method for producing an α,β-unsaturated carboxylic acid through liquid-phase oxidation of an α,β-unsaturated aldehyde with molecular oxygen by using the palladium-containing catalyst of the present invention, an α,β-unsaturated carboxylic acid can be produced in high selectivity or in high productivity.

BEST MODE FOR CARRYING OUT THE INVENTION

The palladium-containing catalyst of the present invention is the one containing 0.001 to 0.40 mole of tellurium metal to 1.0 mole of palladium metal. An α,β-unsaturated aldehyde and an α,β-unsaturated carboxylic acid can be produced from an olefin in high selectivity or in high productivity, or an α,β-unsaturated carboxylic acid can be produced from the α,β-unsaturated aldehyde in high selectivity or in high productivity by subjecting the palladium-containing catalyst to contain tellurium metal in such a predetermined range. In the case that less than 0.001 mole or more than 0.40 mole of tellurium metal to 1.0 mole of palladium metal is contained, an improving effect of selectivity to the α,β-unsaturated aldehyde and the α,β-unsaturated carboxylic acid, or selectivity to the α,β-unsaturated carboxylic acid is insufficient.

To produce a target product in high selectivity, the palladium-containing catalyst preferably contains 0.002 mole or more of tellurium metal to 1.0 mole of palladium metal, more preferably 0.003 mole or more. Further, the palladium-containing catalyst preferably contains 0.30 mole or less of tellurium metal to 1.0 mole of palladium metal, more preferably 0.25 mole or less. To produce a target product in high productivity, the palladium-containing catalyst preferably contains 0.01 mole or more of tellurium metal to 1.0 mole of palladium metal, more preferably 0.03 mole or more. Further, the palladium-containing catalyst preferably contains 0.09 mole or less of tellurium metal to 1.0 mole of palladium metal, more preferably 0.06 mole or less. These contents can be adjusted by a blend ratio of a palladium compound and a tellurium compound to be used in the production of the palladium-containing catalyst, a preparing condition of the catalyst, or the like.

The molar ratio of tellurium metal to palladium metal (Te/Pd) in the palladium-containing catalyst can be calculated from mass and the molecular weight of tellurium metal and palladium metal contained in the palladium-containing catalyst after the preparation. The masses of tellurium metal and palladium metal in the palladium-containing catalyst can be measured by the following method.

Preparation of a Treatment A Liquid

Into a decomposing tube made of Teflon (registered trademark), 0.2 g of a palladium-containing catalyst and the predetermined amounts of concentrated nitric acid, concentrated sulfuric acid and hydrogen peroxide aqueous solution were introduced and a dissolving treatment was carried out with a microwave thermal decomposing device. The resultant sample was filtrated and the filtrate and washing water were altogether filled into a measuring flask and diluted up to the calibration mark to make a treatment A liquid.

Preparation of a Treatment B Liquid

A filter paper on which the insoluble residue of the treatment A was gathered was transferred into a platinum crucible and was heated and burnt to ashes, and lithium methaborate was added to it and fused with a gas burner. After cooled, hydrochloric acid and a small amount of water were added to the crucible to dissolve the fused material. After that, the resultant solution was filled into a measuring flask and diluted up to the calibration mark to make a treatment B liquid.

Each mass of tellurium metal and palladium metal contained in the treatment A liquid and the treatment B liquid was determined quantitatively with ICP emission spectral analyzer, and the total mass of each metal in both the liquids was determined as the mass of tellurium metal and palladium metal in the palladium-containing catalyst.

Further, the palladium-containing catalyst mentioned above may be non-supported type, however, it is preferably supported type in which palladium metal and tellurium metal are supported on a carrier. As the carrier, for example, activated carbon, carbon black, silica, alumina, magnesia, calcia, titania and zirconia can be listed. Among them, activated carbon, silica or alumina is preferable. Preferable specific surface area of the carrier cannot be absolutely fixed because it is variable depending on a kind of carrier, or the like. In the case of activated carbon, the specific surface area is preferably 100 $m^2/g$ or more, more preferably 300 $m^2/g$ or more, and preferably 5,000 $m^2/g$ or less, more preferably 4,000 $m^2/g$ or less. In the case of silica, the specific surface area is preferably 50 $m^2/g$ or more, more preferably 100 $m^2/g$ or more, and preferably 1,500 $m^2/g$ or less, more preferably 1,000 $m^2/g$ or less. As the specific surface area of the carrier becomes smaller, a catalyst in which the effective component (palladium metal) is supported more on its surface can be produced, and as the specific surface area of the carrier becomes larger, a catalyst in which the effective component is supported more can be produced.

The palladium-containing catalyst of the present invention mentioned above can be suitably produced by a method having a step of reducing a compound containing palladium atom in its oxidized state and tellurium atom in its oxidized state by a reducing agent. For example, a method of reducing a palladium compound containing palladium atom in its oxidized state and a tellurium compound containing tellurium atom in its oxidized state by a reducing agent can be listed. Hereinafter, a method for producing the palladium-containing catalyst will be explained.

As the palladium compound containing palladium atom, for example, a palladium salt, palladium oxide or palladium oxide alloy can be listed, and among them, a palladium salt is preferable. As the palladium salt, for example, palladium chloride, palladium acetate, palladium nitrate, palladium sulfate, tetraamminepalladium chloride or palladium bis(acetylacetonate) can be listed, and among them, palladium chloride, palladium acetate, palladium nitrate and tetraamminepalladium chloride are preferable.

As the tellurium compound containing tellurium atom in its oxidized state, for example, a tellurium salt, a telluric acid and a tellurate, a tellurious acid and a tellurite, a tellurium oxide or tellurium oxide alloy can be listed. As the tellurium salt, for example, hydrogen telluride, tellurium tetrachloride, tellurium dichloride, tellurium hexafluoride, tellurium tetraiodide, tellurium tetrabromide or tellurium dibromide can be listed. As the tellurate, for example, sodium tellurate or potassium tellurate can be listed. As the tellurite, for example, sodium tellurite or potassium tellurite can be listed. Among them, the tellurium salt, the telluric acid and the tellurate, the tellurious acid and the tellurite and the tellurium oxide are preferable.

The foregoing palladium compound containing palladium atom in its oxidized state and the foregoing tellurium compound containing tellurium atom in its oxidized state are properly selected and used as raw materials for producing the palladium-containing catalyst. The blend ratio of these compounds is properly selected in such a way that the ratio of palladium metal to tellurium metal in the palladium-containing catalyst becomes a target value. Further, it is possible to use, for example, an oxidized alloy containing both of palladium atom in its oxidized state and tellurium atom in its oxidized state in a predetermined ratio in addition to the above-mentioned method of using the two kinds of compounds.

As the reducing agent to be used in the production of the palladium-containing catalyst, any reducing agents can be used as long as they have the ability at least to reduce palladium atom in its oxidized state and tellurium atom in its oxidized state. For example, ethanol, 2-propanol, formaldehyde, hydrazine, formic acid, oxalic acid, sodium borohydride, lithium aluminum hydride, calcium hydride, hydrogen, ethylene, propylene, 1-butene, 2-butene or isobutylene can be listed. Among them, at least one compound selected from the group consisting of ethanol, 2-propanol, formaldehyde, hydrazine, sodium borohydride, hydrogen, ethylene, propylene, 1-butene, 2-butene and isobutylene is preferable. Two or more kinds of reducing agents can be used in combination.

However, it is preferable to use a compound, as the reducing agent, which does not contain sulfur. Now, the compound which does not contain sulfur means that sulfur element is not contained in the structure of the compound, namely, the compound is not a sulfur-containing compound, and doesn't include the compound which contain sulfur or sulfur containing compounds as small amount of impurities. In the present invention, it is preferable to carry out reduction at relatively low temperature as will be mentioned below, and when a reducing agent which is a sulfur-containing compound is used, sulfur is adsorbed strongly on a carrier, palladium, tellurium or the like and the activity of the resultant palladium-containing catalyst is sometimes lowered.

The reduction may be carried out in gas phase, however, it is preferably carried out in liquid phase. Hereinafter, a method for reducing a palladium compound and a tellurium compound in liquid phase will be explained.

First, a palladium compound and a tellurium compound are dissolved in a solvent, and then the palladium compound and the tellurium compound are reduced by adding a reducing agent. In the case of producing the palladium-containing catalyst of supported type, which will be mentioned later, it is possible to support at least one of the palladium compound and the tellurium compound on a carrier to be used in advance and then to reduce the supported compound. As a result, the target palladium-containing catalyst which contains palladium metal and tellurium metal is precipitated. The method for adding the reducing agent is not particularly limited, however, for example, a method of carrying out reduction by dropping a reducing agent, and a method of carrying out reduction after adding the whole amount of a reducing agent can be listed. The temperature and the reducing time of the system at the time of reduction cannot be absolutely fixed because these are variable depending on the reducing method, the solvent and the reducing agent to be used or the like, and in the case of the liquid-phase reduction method, generally, the reducing temperature is 0 to 100° C. and the reducing time is 0.5 to 24 hours.

As the solvent to be used in the liquid-phase reduction, water is generally used, however, depending on solubilities of the raw materials of palladium and tellurium and the reducing agent or dispersibility of the carrier, an organic solvent such as an alcohol which may be 1-propanol, n-butanol or t-butanol; a ketone which may be acetone, methyl ethyl ketone, methyl isobutyl ketone or cyclohexanone; an organic acid which may be acetic acid, n-valeric acid or isovaleric acid; a hydrocarbon which may be heptane, hexane or cyclohexane, or a mixed solvent of the organic solvent and water can be used.

In the case of preparing the palladium-containing catalyst of supported type, the same procedures of reduction as those mentioned above are carried out except that a carrier is dispersed in the solution containing the palladium compound and the tellurium compound.

However, in the case of preparing the palladium-containing catalyst of activated-carbon supported type, if a solution containing a palladium compound and a tellurium compound is contacted with the carrier (activated carbon) before contacted with a reducing agent, there is a case that the palladium compound and the tellurium compound are reduced and precipitated through a reaction with an active group existing on the outer surface of the carrier and a catalyst having palladium metal and tellurium metal segregated on the outer surface of the carrier is obtained. Therefore, an oxidizing agent such as hydrogen peroxide, nitric acid or hypochlorous acid is preferably existed by a proper amount in the solution containing the palladium compound and the tellurium compound before the solution is contacted with the reducing agent. Now, even in the case of using the carrier, there is a case that the palladium compound and the tellurium compound are reduced by the carrier depending on preparing conditions, however even in such a case, the reduction can also be prevented by subjecting the oxidizing agent to exist in the solution by a proper amount.

The palladium-containing catalyst of the present invention is the one that contains palladium metal and tellurium metal, however, it can also contain one or more of the other metals such as platinum, rhodium, ruthenium, iridium, gold, lead, bismuth, thallium, mercury and carbon. The palladium-containing catalyst can be obtained by carrying out reduction in the coexistence of the metal compound corresponding to the other metal. From the standpoint of realizing high catalyst activity, the total amount of palladium metal and tellurium metal among the metals contained in the palladium-containing catalyst is preferably 25% by mass or more.

Now, the reduction of the palladium compound and the reduction of tellurium compound may be carried out simultaneously in a solution containing both compounds or respective reductions may be carried out in separate steps. In the case of the separate steps, reduction of the palladium compound can be carried out at first, and reduction of the tellurium compound can be also carried out at first. Further, in the case of the separate steps, a kind of the reducing agent, reducing temperature and time, a kind of solvent in the case of liquid-phase reduction or the like can be independently properly set in the respective steps.

In particular, in the case of preparing a catalyst with high activity and high productivity, it is preferable to carry out a reducing step of a compound containing a palladium atom in its oxidized state by a reducing agent previously, and then to carry out a reducing step of a compound containing a tellurium atom in its oxidized state by a reducing agent. In this case, it is preferable to disperse, in a solvent, metallic palladium to be obtained by reducing the palladium compound, and to add to it a solution containing the tellurium compound, and then to reduce the resultant liquid by adding a reducing agent. Besides this method, it is also possible to disperse, in a solvent, palladium metal powder specially obtained, and to add to it a solution containing the tellurium compound, and then to reduce the resultant liquid by adding a reducing agent.

The palladium-containing catalyst (hereinafter, sometimes merely referred to as "catalyst") which was precipitated by reduction is preferably washed with water, solvent or the like. By washing with water, solvent or the like, impurities originated from the palladium compound and the tellurium compound such as chlorides, acetic radicals, nitric radicals and sulfuric radicals can be removed. The method and the number of times of washing is not particularly limited, however, it is preferable to carry out washing to the extent that it can sufficiently remove the impurities because there is a fear that some impurities may inhibit the liquid-phase oxidation reaction of an olefin or an $\alpha,\beta$-unsaturated aldehyde. The washed catalyst is recovered by filtration, centrifugation or the like, and then it may be directly used for the reaction. Further, in the case that the reduction of the palladium compound and the reduction of tellurium compound are carried out respectively in separate steps, it is also preferable to carry out washing between the steps.

Further, the recovered catalyst may be dried. The method of drying is not particularly limited, however, drying is ordinarily carried out by using dryer in air or inert gas. The dried catalyst can be activated, if necessary, before it is used in liquid-phase oxidation reaction. The method of activation is not particularly limited. For example, a method of heat treatment under reductive atmosphere in hydrogen flow can be listed. According to this method, an oxidized film on the surface of palladium metal and impurities which could not be removed by washing can be removed. Physical properties of the prepared catalyst can be confirmed by BET surface area measurement, XRD measurement, CO pulse adsorption method, TEM measurement or the like.

Next, a method for producing an $\alpha,\beta$-unsaturated aldehyde and an $\alpha,\beta$-unsaturated carboxylic acid through liquid-phase oxidation of an olefin with molecular oxygen and a method for producing an $\alpha,\beta$-unsaturated carboxylic acid through liquid-phase oxidation of an $\alpha,\beta$-unsaturated aldehyde with molecular oxygen by using the palladium-containing catalyst of the present invention will be explained.

As the raw olefin, for example, propylene, isobutylene and 2-butene can be listed. Among them, propylene and isobutylene are suitable. The raw olefin may contain a small amount of a saturated hydrocarbon and/or a lower saturated aldehyde as impurities. The $\alpha,\beta$-unsaturated aldehyde and the $\alpha,\beta$-unsaturated carboxylic acid to be produced are those having the same carbon skeleton as the olefin has. Concretely, in the case that the raw material is propylene, acrolein and acrylic acid are obtained, and in the case that the raw material is isobutylene, methacrolein and methacrylic acid are obtained.

As the raw $\alpha,\beta$-unsaturated aldehyde, for example, acrolein, methacrolein, crotonaldehyde ($\beta$-methyl acrolein), and cinnamaldehyde ($\beta$-phenyl acrolein) can be listed. Among them, acrolein and methacrolein are suitable. The raw $\alpha,\beta$-unsaturated aldehyde may contain a small amount of a saturated hydrocarbon and/or a lower saturated aldehyde. The $\alpha,\beta$-unsaturated carboxylic acid to be produced is one in which the aldehyde group of the $\alpha,\beta$-unsaturated aldehyde has changed into the carboxyl group. Concretely, in the case that the raw material is acrolein, acrylic acid is obtained, and in the case that the raw material is methacrolein, methacrylic acid is obtained.

The liquid-phase oxidation reaction may be carried out by any one of a continuous type operation and a batch type operation, however, a continuous type operation is industrially preferable in view of the productivity.

The source of molecular oxygen to be used in the liquid-phase oxidation reaction is preferably air because it is economical, however, pure oxygen or a mixed gas of pure oxygen and air can be used, and if necessary, a mixed gas in which air or pure oxygen is diluted with nitrogen, carbon dioxide, water vapor, or the like can also be used. The gas such as air is ordinarily supplied into a reaction vessel such as autoclave under the pressurized state.

As the solvent to be used in the liquid phase oxidation reaction, for example, it is preferable to use at least one organic solvent selected from the group consisting of t-butanol, cyclohexanol, acetone, methyl ethyl ketone, methyl isobutyl ketone, acetic acid, propionic acid, n-butyric acid, isobutyric acid, n-valeric acid, isovaleric acid, ethyl acetate and methyl propionate. Among them, at least one organic solvent selected from the group consisting of t-butanol, methyl isobutyl ketone, acetic acid, propionic acid, n-butyric acid, isobutyric acid, n-valeric acid and isovaleric acid is more preferable. Further, it is preferable to subject water to coexist with the organic solvent to produce an $\alpha,\beta$-unsaturated aldehyde and an $\alpha,\beta$-unsaturated carboxylic acid or an $\alpha,\beta$-unsaturated carboxylic acid in higher selectivity. The amount of water to be coexisted is not particularly limited, and it is preferably 2% by mass or more to the total mass of the solvent and water, more preferably 5% by mass or more, and preferably 70% by mass or less, more preferably 50% by mass or less. The mixture of the solvent and water is preferably homogeneous, but it may be heterogeneous.

The concentration of the olefin or the $\alpha,\beta$-unsaturated aldehyde which is the raw material of the liquid-phase oxidation reaction is preferably 0.1% by mass or more to the solvent existing in the reactor, more preferably 0.5% by mass or more, and preferably 30% by mass or less, more preferably 20% by mass or less.

The amount of use of the molecular oxygen is preferably 0.1 mole or more to 1 mole of the olefin or the $\alpha,\beta$-unsaturated aldehyde which is the raw material, more preferably 0.2 mole or more, furthermore preferably 0.3 mole or more, and preferably 20 mole or less, more preferably 15 mole or less, furthermore preferably 10 mole or less.

Ordinarily, the catalyst is used in a suspended state in the reaction liquid of the liquid-phase oxidation, however, it may be used in a fixed bed. The amount of use of the catalyst is preferably 0.1% by mass or more to the solution existing in the reactor, more preferably 0.5% by mass or more, furthermore preferably 1% by mass or more, and preferably 30% by mass or less, more preferably 20% by mass or less, furthermore preferably 15% by mass or less.

The reaction temperature and the reaction pressure are properly selected according to the solvent and the raw material to be used. The reaction temperature is preferably 30° C. or more, more preferably 50° C. or more. The reaction temperature is preferably 200° C. or less, more preferably 150° C. or less. Further, the reaction pressure is preferably 0 MPa or more (gauge pressure; hereinafter, every pressure is expressed in gauge pressure), more preferably 0.5 MPa or more. The reaction pressure is preferably 10 MPa or less, more preferably 5 MPa or less.

EXAMPLES

Hereinafter, the present invention will be more concretely explained with reference to Examples and Comparative Examples, however, the present invention is not limited to these Examples. The term "part(s)" in the following Examples and Comparative Examples means part(s) by mass.

(Measurement of the Molar Ratio of Tellurium Metal to Palladium Metal (Te/Pd) in a Catalyst)

This was calculated from the mass and the molecular weight of tellurium metal and palladium metal contained in the catalyst after the preparation. Now, the masses of tellurium metal and palladium metal in the catalyst were measured by the following method.

Preparation of a Treatment A Liquid:

Into a decomposing tube made of Teflon (registered trademark), 0.2 g of a catalyst and the predetermined amounts of concentrated nitric acid, concentrated sulfuric acid and hydrogen peroxide aqueous solution were introduced and a dissolving treatment was carried out with a microwave thermal decomposing device (manufactured by CEM Corporation, MARS5 (trade name)). The resultant sample was filtrated and the filtrate and washing water were altogether filled into a measuring flask and diluted up to the calibration mark to make a treatment A liquid.

Preparation of a Treatment B Liquid:

A filter paper on which the insoluble residue of the treatment A was gathered was transferred into a platinum crucible and was heated and burnt to ashes, and lithium methaborate was added to it and fused with a gas burner. After cooled, hydrochloric acid and a small amount of water were added to the crucible to dissolve the fused material. After that, the resultant solution was filled into a measuring flask and diluted up to the calibration mark to make a treatment B liquid.

Each mass of tellurium metal or palladium metal contained in the treatment A liquid and the treatment B liquid was determined quantitatively with ICP emission spectral analyzer (manufactured by Thermo Elemental Co. Ltd., IRIS-Advantage (trade name)), and the total mass of each metal in both the liquids was determined as the mass of tellurium metal and palladium metal in the catalyst.

(Measurement of Raw Materials, Products and By-products in the Production of an $\alpha,\beta$-unsaturated Aldehyde and an $\alpha,\beta$-unsaturated Carboxylic Acid)

Measurement of raw materials and products in the production of an $\alpha,\beta$-unsaturated aldehyde and an $\alpha,\beta$-unsaturated carboxylic acid was carried out with gas chromatography. Now, conversion of an olefin, selectivity to an $\alpha,\beta$-unsaturated aldehyde to be produced, selectivity to an $\alpha,\beta$-unsaturated carboxylic acid to be produced and selectivity to an $\alpha,\beta$-unsaturated carboxylic acid ester to be produced as a by-product are defined as follows:

Conversion of an olefin (%)=(B/A)×100;

Selectivity to an $\alpha,\beta$-unsaturated aldehyde (%)= (C/B)×100;

Selectivity to an $\alpha,\beta$-unsaturated carboxylic acid (%) (D/B)×100;

Selectivity to an $\alpha,\beta$-unsaturated carboxylic acid ester (%)=(E/B)×100;

Productivity of an $\alpha,\beta$-unsaturated aldehyde (g/g–Pd·h)=F/(I×H); and

Productivity of an $\alpha,\beta$-unsaturated carboxylic acid (g/g–Pd·h)=G/(I×H).

In these formulae, A represents mole number of an olefin supplied, B represents mole number of an olefin reacted, C represents mole number of an $\alpha,\beta$-unsaturated aldehyde produced, D represents mole number of an $\alpha,\beta$-unsaturated carboxylic acid produced, E represents mole number of an $\alpha,\beta$-unsaturated carboxylic acid ester produced as a by-product, F represents mass (unit: g) of an $\alpha,\beta$-unsaturated aldehyde produced, G represents mass (unit: g) of an $\alpha,\beta$-unsaturated carboxylic acid produced, H represents mass (unit: g) of Pd used in the reaction and I represents reaction time (unit: h).

Example 1

(Catalyst Preparation)

To 10.0 parts of a silica carrier (specific surface area: 450 m²/g; pore volume: 0.68 cc/g), an aqueous solution obtained by dissolving 0.011 part of telluric acid in 6.8 parts of pure water was added little by little and shaken while these operations were repeated. The resultant mixture was kept at 100° C. in air for 3 hours, and then it was calcined at 400° C. in air for 3 hours to obtain a telluric acid supported silica carrier.

Meanwhile, 1.1 parts of palladium acetate (manufactured by N. E. Chemcat Corporation) was dissolved in 10.0 parts of acetic acid to prepare an acetic acid solution. The acetic acid solution thus prepared was added to the above-mentioned telluric acid supported silica carrier little by little and shaken while these operations were repeated. When the amount of the acetic acid solution equivalent to the total pore volume was added, once, evaporation of the system was carried out. The remainder of the acetic acid solution was treated in the same way, namely, added little by little and shaken and these operations were repeated and evaporation of the system was carried out. Subsequently, the system was calcined at 450° C. in air for 3 hours. The silica carrier thus obtained was added to 25 parts of 37% by mass formaldehyde aqueous solution. Then the system was heated to 70° C., kept at 70° C. for 2 hours while stirred, filtrated under reduced pressure and filtrated while washed with 1,000 parts of hot water. Thereafter, the resultant system was dried at 100° C. for 2 hours under nitrogen flow to obtain a palladium-containing catalyst of silica-suppported type on which palladium metal and tellurium metal were supported. Te/Pd in the catalyst was 0.01.

(Evaluation of Reaction)

The total amount of the catalyst obtained by the above-mentioned method and 75 parts of 75% by mass t-butanol aqueous solution as a reaction solvent were introduced into an autoclave and the autoclave was shut tight. Subsequently, 4.0 parts of isobutylene was introduced into it, and the system was stirred (number of revolutions: 1,000 rpm) and heated to 90° C. After the heating was finished, nitrogen was introduced into the autoclave to the internal pressure of 2.4 MPa and then compressed air was introduced into it to the internal pressure of 4.8 MPa. When the internal pressure dropped by 0.1 MPa (the internal pressure: 4.7 MPa) during the reaction, oxygen was introduced into it by 0.1 MPa, and this operation was repeated 9 times. The internal pressure right after the introduction of oxygen was 4.8 MPa. After the ninth introduction of air, when the internal pressure was 4.7 MPa, the reaction was finished. The reaction time was 90 minutes.

After the reaction was finished, the inside of the autoclave was cooled by ice bath. A gas-sampling bag was attached to the gas outlet of the autoclave and the gas outlet was opened and the emerging gas was collected while the internal pressure of the reactor was released. The reaction liquid containing catalyst was taken out from the autoclave and the catalyst was separated with membrane filter and the reaction liquid was recovered. The recovered reaction liquid and the sampled gas were analyzed by gas chromatography and the conversion and selectivity were calculated.

Example 2

(Catalyst Preparation)

The same procedure as in Example 1 was carried out except that the amount of telluric acid used was changed to 0.055 part, and a palladium-containing catalyst of silica-supported type on which palladium metal and tellurium metal were supported was obtained. Te/Pd in the catalyst was 0.05.

(Evaluation of Reaction)

Using the catalyst obtained above, the same procedure as in Example 1 was carried out.

Example 3

(Catalyst Preparation)

Step 1:

In 60 parts of 88% by mass n-valeric acid aqueous solution, 1.1 parts of palladium acetate (manufactured by N. E. Chemcat Corporation) was dissolved under heating. To this solution, 5.0 parts of an activated carbon (specific surface area: 780 m$^2$/g) was added and the resultant mixture was introduced into an autoclave and the autoclave was shut tight. The system was stirred and temperature of the internal liquid was cooled to 10° C. or less, and then propylene gas was introduced into it to the internal pressure of 0.5 MPa and the system was kept at 50° C. for 1 hour. After it was kept for 1 hour, the temperature of the internal liquid was cooled to 20° C. or less, and then the internal pressure was released. The system was filtrated under reduced pressure, washed by pure water several times and dried at 100° C. for 2 hours under nitrogen flow to obtain a palladium-containing catalyst of activated carbon-supported type on which palladium metal was supported.

Step 2:

The catalyst obtained in the step 1 was added to 40 parts of pure water and the resultant mixture was stirred for 15 minutes. Further, an aqueous solution obtained by dissolving 0.055 part of telluric acid in 10 parts of pure water was added, and kept at 100° C. for 1 hour while stirred. The resultant liquid was evaporated to dryness and 1.9 parts of 37% by mass formaldehyde aqueous solution was added to it and, to the resultant system, 30% by mass potassium hydroxide aqueous solution was dropped to adjust pH of the system to about 9.0. The resultant system was kept at room temperature overnight, and filtrated under reduced pressure and filtrated while washed with 1,000 parts of hot water. Thereafter, the resultant system was dried at 100° C. for 2 hours under nitrogen flow to obtain a palladium-containing catalyst of activated carbon-supported type on which palladium metal and tellurium metal were supported. Te/Pd in the catalyst was 0.05.

(Evaluation of Reaction)

Using the catalyst obtained above, the same procedure as in Example 1 was carried out except that oxygen was introduced 5 times.

Example 4

(Catalyst Preparation)

The same procedure as in Example 1 was carried out except that the amount of telluric acid used was changed to 0.11 part, and a palladium-containing catalyst of silica-supported type on which palladium metal and tellurium metal were supported was obtained. Te/Pd in the catalyst was 0.1.

(Evaluation of Reaction)

Using the catalyst obtained above, the same procedure as in Example 1 was carried out.

Example 5

(Catalyst Preparation)

The same procedure as in Example 1 was carried out except that the amount of telluric acid used was changed to 0.275 part, and a palladium-containing catalyst of silica-supported type on which palladium metal and tellurium metal were supported was obtained. Te/Pd in the catalyst was 0.25.

(Evaluation of Reaction)

Using the catalyst obtained above, the same procedure as in Example 1 was carried out.

Example 6

(Catalyst Preparation)

The same procedure as in Example 1 was carried out except that the amount of telluric acid used was changed to 0.363 part, and a palladium-containing catalyst of silica-supported type on which palladium metal and tellurium metal were supported was obtained. Te/Pd in the catalyst was 0.33.

(Evaluation of Reaction)

Using the catalyst obtained above, the same procedure as in Example 1 was carried out except that oxygen was introduced 5 times.

Comparative Example 1

(Catalyst Preparation)

In 10.0 parts of acetic acid, 1.1 parts of palladium acetate (manufactured by N. E. Chemcat Corporation) was dissolved. The acetic acid solution was added little by little to 10.0 parts of a silica carrier (specific surface area: 450 m$^2$/g; pore volume: 0.68 cc/g) and shaken while these operations were repeated. When the amount of the acetic acid solution equivalent to about the total pore volume was added, once, evaporation of the system was carried out. The remainder of the acetic acid solution was treated in the same way, namely, added little by little and shaken and these operations were repeated and, after the whole amount of the acetic acid solution was added, evaporation of the system was carried out. Subsequently, the system was calcined at 450° C. in air for 3 hours. The silica carrier thus obtained was added to 25 parts of 37% by mass formaldehyde aqueous solution. Then the system was heated to 70° C., kept at 70° C. for 2 hours while stirred, filtrated under reduced pressure and filtrated while washed with 1,000 parts of hot water. Thereafter, the resultant system was dried at 100° C. for 2 hours under nitrogen flow to obtain a palladium-containing catalyst of silica-supported type on which palladium metal was supported.

(Evaluation of Reaction)

Using the catalyst obtained above, the same procedure as in Example 1 was carried out.

Comparative Example 2

(Catalyst Preparation)

The same procedure as in the step 1 of Example 3 was carried out and a palladium-containing catalyst of activated carbon-supported type on which palladium metal was supported was prepared.

(Evaluation of Reaction)

Using the catalyst obtained above, the same procedure as in Example 1 was carried out except that oxygen was introduced 5 times.

Comparative Example 3

(Catalyst Preparation)

The same procedure as in Example 1 was carried out except that the amount of telluric acid used was changed to 0.55 part, and a palladium-containing catalyst of silica-supported type on which palladium metal and tellurium metal were supported was obtained. Te/Pd in the catalyst was 0.5.

(Evaluation of Reaction)

Using the catalyst obtained above, the same procedure as in Example 1 was carried out.

The results of the above are shown in Table 1. It was found that methacrolein and methacrylic acid can be produced in high selectivity by using the palladium-containing catalyst of the present invention.

formaldehyde aqueous solution. In order to reduce tellurium, the system was heated to 70° C., kept at 70° C. for 2 hours while stirred, filtrated under reduced pressure and filtrated while washed with water to obtain a palladium-containing catalyst of silica-supported type on which palladium metal and tellurium metal were supported. Molar ratio of Te/Pd in the catalyst was 0.030.

(Evaluation of Reaction)

Into an autoclave, 10.99 parts of the catalyst obtained by the above-mentioned method, 100 parts of 75% by mass t-butanol aqueous solution as reaction solvent and 0.02 part of p-methoxyphenol were introduced and the autoclave was shut tight. Subsequently, 2.75 parts of isobutylene was introduced into it, and the system was stirred (number of revolutions: 1,000 rpm) and heated to 90° C. After the heating was finished, nitrogen was introduced into the autoclave to the internal pressure of 2.3 MPa and then compressed air was introduced into it to the internal pressure of 4.6 MPa. When the internal pressure dropped by 0.1 MPa during the reaction, oxygen was introduced into it to increase the internal pressure

TABLE 1

|  | Te/Pd | Reaction time (min) | Conversion of isobutylene (%) | Selectivity to methacrolein (%) | Selectivity to methacrylic acid (%) | Selectivity to methacrolein + methacrylic acid (%) | Selectivity to methallyl methacrylate (%) |
|---|---|---|---|---|---|---|---|
| Ex. 1 | 0.01 | 90 | 49.3 | 55.1 | 20.5 | 75.6 | 0.8 |
| Ex. 2 | 0.05 | 110 | 50.2 | 49.6 | 27.8 | 77.4 | 1.2 |
| Ex. 3 | 0.05 | 210 | 28.1 | 62.3 | 18.9 | 81.2 | 3.6 |
| Ex. 4 | 0.1 | 120 | 50.5 | 45.2 | 36.8 | 82.0 | 2.3 |
| Ex. 5 | 0.25 | 300 | 48.7 | 46.2 | 35.1 | 81.3 | 4.7 |
| Ex. 6 | 0.33 | 300 | 28.7 | 33.7 | 45.0 | 78.7 | 5.2 |
| Comp. Ex. 1 | 0 | 70 | 50.9 | 45.2 | 20.2 | 65.4 | 0.5 |
| Comp. Ex. 2 | 0 | 100 | 28.8 | 44.8 | 20.5 | 65.3 | 2.3 |
| Comp. Ex. 3 | 0.5 | 240 | 7.0 | 32.2 | 5.2 | 37.4 | 10.2 |

Example 7

(Catalyst Preparation)

Step 1:

In 60 parts of pure water, 6.46 parts of palladium nitrate (manufactured by N. E. Chemcat Corporation; palladium content: 23.21% by mass) was dissolved to prepare an mixed solution. The mixed solution thus obtained was impregnated into 30.0 parts of a silica carrier (specific surface area: 450 m$^2$/g; pore volume: 0.68 cc/g) and the system was evaporated. Thereafter, the system was calcined at 200° C. in air for 3 hours. The silica carrier thus obtained was added to 90 parts of 37% by mass formaldehyde aqueous solution. Then the system was heated to 70° C., kept at 70° C. for 2 hours while stirred, filtrated under reduced pressure and filtrated while washed with 1,000 parts of hot water to obtain a palladium-containing catalyst of silica-supported type on which palladium metal was supported.

Step 2:

One-third by mass of the palladium-containing catalyst of silica-supported type obtained by the foregoing preparing procedure was dispersed in 50 parts of water and, to the dispersion, a solution obtained by dissolving 0.054 part of telluric acid in 10 parts of pure water was dropped and the resultant mixture was added to 1.9 parts of 37% by mass by 0.1 MPa, and this operation was repeated 10 times. After the tenth introduction of oxygen, when the internal pressure was dropped by 0.1 MPa, the reaction was finished. The reaction time was 46 minutes.

After the reaction was finished, the inside of the autoclave was cooled by ice bath. A gas-sampling bag was attached to the gas outlet of the autoclave, and the gas outlet was opened and the emerging gas was collected while the internal pressure of the reactor was released. The reaction liquid containing catalyst was taken out from the autoclave and the catalyst was separated with membrane filter and the reaction liquid was recovered. The recovered reaction liquid and the sampled gas were analyzed by gas chromatography and the conversion, the selectivity and the productivity were calculated.

Example 8

The same procedure of the catalyst preparation as in Example 7 was carried out except that the reduction temperature of tellurium was 90° C. and the amount of the catalyst introduced into the autoclave was 10.81 parts, and a palladium-containing catalyst of silica-supported type on which palladium metal and tellurium metal were supported was obtained. Molar ratio of Te/Pd in the catalyst was 0.041. Using this catalyst, the same procedure of reaction as in Example 7 was carried out.

Example 9

The same procedure of the catalyst preparation as in Example 7 was carried out except that the reduction temperature of tellurium was the reflux temperature and the amount of the catalyst introduced into the autoclave was 10.65 parts, and a palladium-containing catalyst of silica-supported type on which palladium metal and tellurium metal were supported was obtained. Molar ratio of Te/Pd in the catalyst was 0.043. Using this catalyst, the same procedure of reaction as in Example 7 was carried out.

Example 10

The same procedure of the catalyst preparation as in Example 7 was carried out except that the amount of telluric acid was 0.216 part, the amount of 37% by mass formaldehyde aqueous solution was 7.60 parts and the amount of the catalyst introduced into the autoclave was 10.99 parts, and a palladium-containing catalyst of silica-supported type on which palladium metal and tellurium metal were supported was obtained. Molar ratio of Te/Pd in the catalyst was 0.048. Using this catalyst, the same procedure of reaction as in Example 7 was carried out.

Example 11

The same procedure of the catalyst preparation as in Example 7 was carried out except that the reduction temperature of tellurium was the reflux temperature, the amount of telluric acid was 0.108 part, the amount of 37% by mass formaldehyde aqueous solution was 3.80 parts and the amount of the catalyst introduced into the autoclave was 10.84 parts, and a palladium-containing catalyst of silica-supported type on which palladium metal and tellurium metal were supported was obtained. Molar ratio of Te/Pd in the catalyst was 0.067. Using this catalyst, the same procedure of reaction as in Example 7 was carried out.

Example 12

The same procedure of the catalyst preparation as in Example 7 was carried out except that the reduction temperature of tellurium was the reflux temperature, the amount of telluric acid was 0.054 part, the amount of 37% by mass formaldehyde aqueous solution was 1.90 parts and the amount of the catalyst introduced into the autoclave was 10.65 parts, and a palladium-containing catalyst of silica-supported type on which palladium metal and tellurium metal were supported was obtained. Molar ratio of Te/Pd in the catalyst was 0.105. Using this catalyst, the same procedure of reaction as in Example 7 was carried out.

Comparative Example 4

The same procedure of preparation as in the step 1 of Example 7 was carried out, and a palladium-containing catalyst of silica-supported type on which palladium metal was supported was obtained. Using this catalyst, the same procedure of reaction as in Example 7 was carried out.

The results of the above are shown in Table 2. It was found that methacrolein and methacrylic acid can be produced in high selectivity by using the palladium-containing catalyst of the present invention.

TABLE 2

| | Te/Pd | Reaction time (min) | Conversion of isobutylene (%) | Selectivity to methacrolein (%) | Selectivity to methacrylic acid (%) | Selectivity to methacrolein + methacrylic acid (%) | Productivity of methacrolein (g/g-Pd · h) | Productivity of methacrylic acid (g/g-Pd · h) | Productivity of methacrolein + methacrylic acid (g/g-Pd · h) |
|---|---|---|---|---|---|---|---|---|---|
| Ex. 7 | 0.030 | 46 | 94.8 | 17.7 | 40.0 | 57.7 | 1.4 | 4.0 | 5.4 |
| Ex. 8 | 0.041 | 29 | 92.3 | 17.1 | 40.0 | 57.1 | 2.2 | 6.3 | 8.5 |
| Ex. 9 | 0.043 | 33 | 91.1 | 18.2 | 41.1 | 59.3 | 2.0 | 5.7 | 7.7 |
| Ex. 10 | 0.048 | 30 | 92.4 | 18.5 | 39.7 | 58.2 | 2.2 | 5.9 | 8.1 |
| Ex. 11 | 0.067 | 52 | 94.0 | 10.4 | 50.5 | 60.9 | 0.8 | 4.5 | 5.3 |
| Ex. 12 | 0.105 | 175 | 90.6 | 12.0 | 61.7 | 73.7 | 0.3 | 1.6 | 1.9 |
| Comp. Ex. 4 | 0 | 51 | 90.4 | 26.1 | 29.3 | 55.4 | 1.8 | 2.4 | 4.2 |

What is claimed is:

1. A method for producing an $\alpha,\beta$-unsaturated aldehyde and an $\alpha,\beta$-unsaturated carboxylic acid through liquid-phase oxidation of an olefin with molecular oxygen using a palladium-containing catalyst comprising 0.001 to 0.40 mole of tellurium metal to 1.0 mole of palladium metal.

2. The method according to claim 1, wherein the palladium metal and the tellurium metal are supported on a carrier.

3. The method according to claim 1, wherein said catalyst comprises 0.01 to 0.09 mole of tellurium metal to 1.0 mole of palladium metal.

4. The method according to claim 3, wherein the palladium metal and the tellurium metal are supported on a carrier.

5. The method according to claim 1, wherein said catalyst comprises 0.003 to 0.25 mole of tellurium metal to 1.0 mole of palladium metal.

6. The method according to claim 5, wherein the palladium metal and the tellurium metal are supported on a carrier.

7. A method for producing an $\alpha,\beta$-unsaturated carboxylic acid through liquid-phase oxidation of an $\alpha,\beta$-unsaturated aldehyde with molecular oxygen using a palladium-containing catalyst comprising 0.001 to 0.40 mole of tellurium metal to 1.0 mole of palladium metal.

8. The method according to claim 7, wherein the palladium metal and the tellurium metal are supported on a carrier.

9. The method according to claim 7, wherein said catalyst comprises 0.01 to 0.09 mole of tellurium metal to 1.0 mole of palladium metal.

10. The method according to claim 9, wherein the palladium metal and the tellurium metal are supported on a carrier.

11. The method according to claim 7, wherein said catalyst comprises 0.003 to 0.25 mole of tellurium metal to 1.0 mole of palladium metal.

12. The method according to claim 11, wherein the palladium metal and the tellurium metal are supported on a carrier.

* * * * *